Nov. 7, 1967 W. D. KRAUSE Plant Pat. 2,775
NECTARINE TREE
Filed Sept. 12, 1966
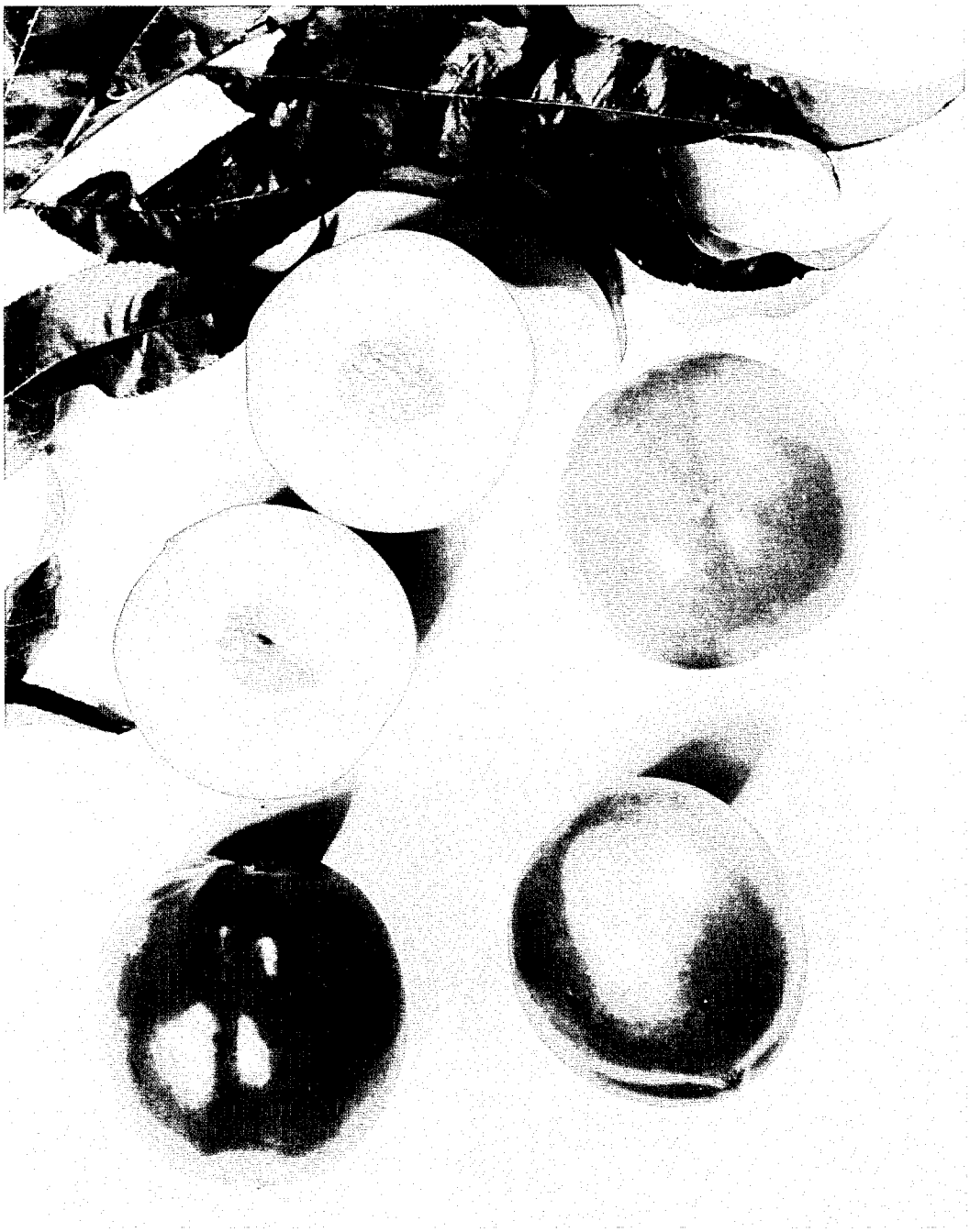
INVENTOR
Walter D. Krause
BY Webster & Webster
ATTORNEYS United States Patent Office Plant Pat. 2,775
Patented Nov. 7, 1967

2,775
NECTARINE TREE

Walter D. Krause, Fresno, Calif., assignor to Stribling's Nurseries, Inc., Merced, Calif., a corporation of California Filed Sept. 12, 1966, Ser. No. 578,898
1 Claim. (Cl. Plt.—41)

This invention relates to a new and distinct variety of nectarine tree which bears high quality, visually attractive, early ripening, yellow-flesh fruit having yellow skin substantially completely overspread with red.

The instant variety of nectarine tree is characterized by a tree which is uniformly vigorous, bears regularly, and is quite productive over the entire fruit-bearing area of the tree.

The variety is further characterized—in comparison to the Red June nectarine (United States Plant Patent No. 2,044), which it most nearly resembles in the general appearance of the fruit and having the same harvest season—by fruit with firmer flesh, a more brilliant red exterior color, larger average size, and better eating quality.

The herein claimed variety of nectarine tree was originated by me, as an open pollinated seedling of the Sun Grand nectarine (United States Plant Patent No. 974), in an experimental orchard located at Merced, Merced County, Calif.; such experimental orchard being under my control and direction, and the variety was at all times maintained under close observation by me.

When the variety came into bearing and I recognized the excellent quality of the early ripening fruit and its excellent appearance—especially desirable for the early fresh fruit market—I selected the variety for asexual reproduction. Such asexual reproduction of the tree was then accomplished by me, by budding on S-37 rootstock (United States Plant Patent No. 904), in the aforesaid experimental orchard; the reproductions, in maturity, having run true to the parent tree in all respects.

The drawing comprises an illustration, by photographic reproduction in color, of a twig with leaves, three whole fruit, and another fruit cut in half to show the flesh and with the stone remaining in one half.

Referring now more specifically to the pomological details of this new and distinct variety of nectarine tree, the following is an outline description thereof; all major color plate identifications being by reference to Maerz and Paul Dictionary of Color, except where common terms of color definition are employed.

Tree:
- *Vigor.*—Uniformly vigorous.
- *Growth.*—Medium.
- *Structure.*—Medium.
- *Form.*—Spreading.
- *Production.*—Productive.
- *Bearing.*—Regular bearer.

Trunk:
- *Sturdiness.*—Sturdy; well developed.
- *Texture.*—Exterior bark—finely checked. Medium depth.
- *Color.*—Dull brown-gray.

Branches:
- *Strength.*—Strong.
- *Branch unions.*—Strong.
- *Color.*—Slightly lighter brown than trunk.
- *Lenticels.*—
  Number—few, evenly dispersed. Size—small.

Leaves:
- *Size.*—Large. Vigorous growth of tree exhibits an abundance of broad, deep green leaves. Average length—6½". Average width—1⅝".
- *Form.*—Lanceolate.
- *Thickness.*—Medium.
- *Texture.*—Top side—glossy. Under side—dull.
- *Margin.*—Evenly crenate.
- *Petiole.*—Average ⅜" to ½" in length.
- *Glands.*—Average number—2. Globose; positioned on petiole and base of leaf.
- *Stipules.*—None.
- *Pubescene.*—None.
- *Color.*—Top side—glossy deep green (23-L-7). Under side—lighter dull green (22-L-6).

Flower buds:
- *Chilling requirements.*—800 hour class.
- *Size.*—Large.
- *Form.*—Well filled; slightly pointed on apex prior to opening.
- *Stem.*—Sturdy. Average length—¼" from twig to base of bud.
- *Color.*—Light pink.

Flowers:
- *Blooming period.*—Date of first bloom—on or about March 7th. Date of full bloom—on or about March 9th. Medium, as compared with other commercial nectarine varieties.
- *Size.*—Large.
- *Color.*—Petals are light pink with deep maroon shade at the base.
- *Fertility.*—Self-fertile.

Fruit:
- *Maturity when described.*—Firm ripe—June 3, 1966.
- *Date of first fruit maturity.*—Firm ripe—June 3, 1966. Variable, dependent on season—from June 3rd to June 14th.
- *Date of last fruit maturity.*—Firm ripe—June 13, 1966. Variable, dependent on season—from June 13th to June 20th.
- *Size.*—Large. Average diameter axially—2½". Average transversely in suture plane—2¼".
- *Form.*—Perpendicular to the suture line, the fruit is symmetrical. One side of each fruit slightly larger than the opposite, particularly before fruit is fully matured. At full maturity, the sides are nearly equal.
- *Suture.*—Extends from base to pistil point in a distinct line and slight indentation. Slight depression extends from pistil point over area opposite the suture line.
- *Ventral surface.*—Rounded; broad at base; both sides equal.
- *Cavity.*—Slightly elongated; flared; suture line is distinct. Average depth—5/16". Average breadth—½". Average length—¾".
- *Base.*—Uniform; well rounded.
- *Apex.*—Slightly elongated.
- *Pistil point.*—Small.

Skin:
- *Thickness.*—Medium.
- *Texture.*—Durable.
- *Tenacity.*—Tenacious to flesh at all stages of maturity.
- *Tendency to crack.*—None noted.
- *Color.*—Rich yellow (9-L-5) ground color substantially completely (about 80%) overspread with glossy brilliant red (4-L-10) at firm-ripe maturity.

Flesh:
- *Amygdalin.*—None.
- *Juice.*—Moderate at firm-ripe maturity.
- *Texture.*—Firm but melting; withstands handling without cell breakage.
- *Fibers.*—Few; white; fine; tender.

*Ripens.*—From outside toward the pit.

*Flavor.*—Has a distinctive fruity flavor which is subacid and slightly spicy.

*Aroma.*—Pronounced; pleasant; readily associated with the fruit flavor.

*Eating quality.*—Good.

*Color.*—Bright yellow (9–L–5).

*Surface of pit cavity.*—Yellow, without pink or red pigmentation.

Stone:

*Type.*—Semi-freestone at firm-ripe maturity. Freestone at soft-ripe maturity. Fibers remain attached to stone at firm-ripe maturity.

*Size.*—Medium. Average length—1⅜". Average breadth—⅞". Average thickness—⅝".

*Form.*—Oblong.

*Base.*—Irregularly cuneate.

*Hilum.*—Oblong; narrow; indented.

*Apex.*—Acuminate; sharp pointed.

*Sides.*—Unequal.

*Surface.*—Irregularly furrowed and pitted.

*Ridges.*—Both sides; interrupted; slightly rounded.

*Ventral edge.*—Thin; irregular; disappearing near apex.

*Tendency to split.*—None.

*Color.*—Tan to very light brown. Ridge surfaces—light tan.

Use: Dessert. Market—local and long distance shipping.

Growing type: Commercial; home orchard.

Keeping quality: Excellent. Retains firmness and appearance during handling and shipping. Matures and ripens to melting texture for use.

Shipping quality: Excellent; fruit texture resists bruises.

Resistance to disease: Average, as compared to other varieties. Susceptible to powdery mildew in very humid environment.

The tree and its fruit herein described may vary in slight detail due to climatic and soil conditions under which the variety may be grown; the present description being of the variety as grown in the Central Valley of California.

The following is claimed:

A new and distinct variety of nectarine tree, substantially as illustrated and described, characterized by its uniform vigor and regular, productive bearing of early ripening, firm yellow-flesh fruit having yellow skin substantially completely overspread with red; and further characterized by fruit which, while having the general appearance and same harvest period as the Red June nectarine, has firmer flesh, a more brilliant red exterior color, large avorage size, and better eating quality.

No references cited.

ROBERT E. BAGWILL, *Primary Examiner.*